(12) United States Patent
Hidaki et al.

(10) Patent No.: US 6,177,109 B1
(45) Date of Patent: Jan. 23, 2001

(54) METHOD FOR PRODUCING FOOD PRODUCT OF WHEAT HAVING IMPROVED QUALITY AND PRESERVABILITY

(75) Inventors: Yumiko Hidaki, Koka-gun; Hirokazu Tani, Kanzaki-gun; Yasuhiro Shimizu, Hikone, all of (JP)

(73) Assignee: Daiwa Kasei Kabushiki Kaisha (JP)

( * ) Notice: Under 35 U.S.C. 154(b), the term of this patent shall be extended for 0 days.

(21) Appl. No.: 09/371,866

(22) Filed: Aug. 5, 1999

(30) Foreign Application Priority Data

Aug. 10, 1998 (JP) .................................. 10-226225

(51) Int. Cl.⁷ ....................................... A21D 2/26
(52) U.S. Cl. .................. 426/20; 426/28; 426/27
(58) Field of Search ................. 426/20, 27, 28, 426/18, 549, 555, 556

(56) References Cited

U.S. PATENT DOCUMENTS

| 4,237,230 | 12/1980 | Iida et al. | 435/207 |
| 4,522,832 | 6/1985 | Morrison | 426/20 |

FOREIGN PATENT DOCUMENTS

| 2511847 | 9/1976 | (DE) . |
| 3-58141755 * | 8/1983 | (JP) . |
| 04207143 | 11/1990 | (JP) . |
| 431853 * | 11/1974 | (SU) . |

OTHER PUBLICATIONS

Database Fsta 'Online!' International Food Information Service (IFIS) Frankfurt/Main, DE Drobot V I et al.: "Use of Nb–galactosidase for treating dried skim milk in baking." Database accession No. 83 – 4 – 08–p1257 XP002123183 *abstract* & Pishchevaya Promyshlennost, 1982, KTIPP, USSR.

* cited by examiner

Primary Examiner—Keith D. Hendricks
(74) Attorney, Agent, or Firm—Baker Botts L.L.P.

(57) ABSTRACT

A method for producing a food product of wheat includes the step of adding a bacillus lactase enzyme having activity for transferring sugar to lipid to raw material of wheat, where the food product of wheat produced by the method maintains its freshness for a longer period of time than a food product of wheat produced by a method including no step of adding the enzyme to the material.

7 Claims, 1 Drawing Sheet

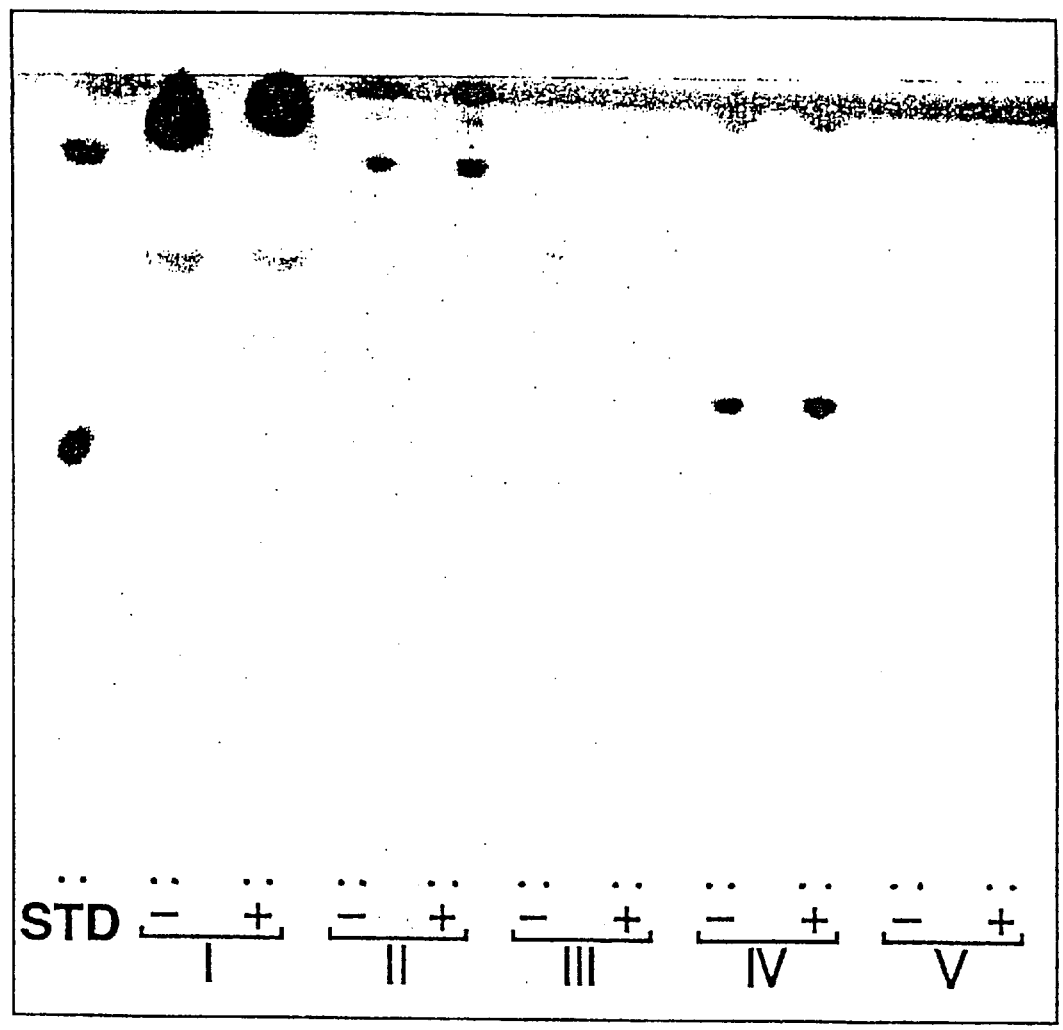
FIGURE

US 6,177,109 B1

METHOD FOR PRODUCING FOOD PRODUCT OF WHEAT HAVING IMPROVED QUALITY AND PRESERVABILITY

BACKGROUND OF THE INVENTION

1. Field of the Invention

The present invention relates to a method for producing food products of wheat capable of maintaining freshness for a long period of time.

2. Description of the Related Art

The quality of food products of wheat such as bread deteriorates over time after the production. For example, in the case of bread, the retrogradation after baking and the reduction of a moisture content by evaporation are responsible for the deterioration of the quality of bread over time.

In the prior art, for the purpose of preventing the quality deterioration over time, a larger amount of water within a defined acceptable range or an emulsifier such as monoglyceride (MG) is added to bread dough; the retrogradation of starch contained in wheat flour is controlled through partial breakdown of starch by $\alpha$-amylase or the like; and the like.

Effects of addition of water to dough vary depending on the difference between the lots of wheat flour used as a raw material. When using wheat flour of the kind having a large water-absorbing ability, the dough becomes so sticky that ease of handling, production yield and the like may be reduced.

The added emulsifier does not have so much effect on the prevention of the retrogradation. The addition of a large amount of the emulsifier results in an emulsion odor, which impairs preferable aroma and flavor inherent in bread that are obtained by fermentation and baking. The addition of the emulsifier is likely to cause bread to become like a gum, which leads to bad mastication.

It has been confirmed that the addition of an enzyme for breaking down starch, such as $\alpha$-amylase, provides increased volume which makes soft crumb, and prevents the retrogradation through partial breakdown of amylose. In this case, however, there are still problems that the dough is slack and that the retrogradation of crumb texture is not satisfactorily prevented. An addition of various hydrolyzing enzymes for improving the quality of bread, such as the starch hydrolyzing enzyme, break down ingredients of wheat flour such as starch. However, excessive breakdown of the ingredients of wheat flour is damaging thereto. Thus, the use of the hydrolyzing enzymes requires a large amount of know-how and strict control of the production process, and/or other optional additives for preventing excessive breakdown of the ingredients of wheat flour.

Examples of other hydrolyzing enzymes include lactase ($\beta$-galactosidase) (for example, see Japanese Laid-Open Publication No. 4-207143). However, the use of lactase is not usual (see D. Every, Food Technology in New Zealand, May 1990, p. 19). Lactase splits lactose into glucose and galactose. Glucose is fermentable, and thus may increase product volume. On the other hand, galactose is non-fermentable, but it is believed that it is available for Maillard reactions, and thus improves flavor and color.

Wheat flour naturally contains glycolipids in small amounts, some of which are useful for improving the quality of food products of wheat such as bread. Examples of glycolipids of which the usefulness has been known include monogalactosyldiglyceride (MGDG) and digalactosyldiglyceride (DGDG). These glycolipids are called glyceroglycolipid.

The above-described glycolipids are coupled, for example, in bread to both starch and gluten which form the skeleton of the bread, forming barriers and improving gas and moisture retention properties. The utilization of the above characteristic feature of the glycolipids might enable bread and the like to maintain its freshness for a long period of time. However, the amounts of such glycolipids in wheat flour are very small, and vary among different types or lots of wheat flour. Accordingly, it is difficult to improve the quality of food products of wheat such as bread by utilizing such a characteristic feature of glycolipids naturally contained in wheat flour.

SUMMARY OF THE INVENTION

The present invention is provided for solving the above-described problems. We place importance on the role of glycolipids in the quality improvement of food products of wheat. We believed that if glycolipids could be enhanced in the producing process of food products of wheat such as bread, it would have provided the food products with satisfactory properties. Subsequently, a method for enhancing glycolipids has been studied by us. As a result, we found out that when certain enzymes activating a transfer of sugar to lipid (e.g., lactase), and optionally sugar such as lactose and lipid such as glycerides, are added to a raw material of a food product of wheat such as bread, glycolipids useful for maintaining freshness of the food product of wheat is generated and enhanced, and a very satisfactory food product of wheat can be therefore obtained. Then, we achieved the invention.

According to the present invention, a method for producing a food product of wheat includes the step of adding an enzyme having activity for transferring sugar to lipid to raw material of the food product of wheat, where the food product of wheat produced by the method maintains its freshness for a longer period of time than a food product of wheat produced by a method including no step of adding the enzyme to the material.

In one embodiment of the present invention, the enzyme having activity for transferring sugar to lipid is lactase.

In one embodiment of the present invention, the lactase is derived from a microorganism of the genus Bacillus.

In one embodiment of the present invention, the microorganism of the genus Bacillus is *Bacillus circulans*.

In one embodiment of the present invention, the method further includes the step of adding lipids to the raw material of the food product of wheat.

In one embodiment of the present invention, the method further includes the step of adding lactose to the raw material of the food product of wheat.

In one embodiment of the present invention, the food product of wheat is selected from the group consisting of breads, noodles, confectioneries, fried products with breadcrumbs, and fried products with tempura flour.

In one embodiment of the present invention, the food product of wheat is a bread.

Thus, the invention described herein makes possible the advantage of providing a method for producing food products of wheat capable of maintaining freshness for a long period of time.

This and other advantages of the present invention will become apparent to those skilled in the art upon reading and understanding the following detailed description with reference to the accompanying figure.

BRIEF DESCRIPTION OF THE DRAWINGS

The FIG. 1 is a diagram showing a result of thin layer chromatography analysis of glycolipids in bread acted on by lactase.

DESCRIPTION OF THE PREFERRED EMBODIMENTS

The present invention is achieved based on the findings that such glycolipids, preferably glycerolipids, that are generated by an enzyme such as lactase transferring sugar to lipid improves the quality of food products of wheat such as bread.

Glycerolipid is a generic name of gycolipid having carbohydrate (sugar) as a hydrophilic group, and diacylglycerol, alkylacylglycerol, or alkenylacylglycerol as a fat-soluble (non-polar) group.

In the method of the present invention, any enzyme having the activity for transferring sugar to lipid can be used. Examples of known enzymes that catalyze a transfer reaction of sugar to lipid include galactosidase derived from *Escherichia coli*, invertase derived from *Saccharomyces cerevisiae*, and xylosidase derived from *Aspergillus niger* (see Japanese Laid-Open Publication No. 6-70789). Lactase derived from *Bacillus circulans* is more preferable. Lactase derived from Bacillus circulans LOB 377 strain (ATCC No. 31382; see U.S. Pat. No. 4,237,230) is commercially available from Daiwa Fine Chemicals Co., Ltd., of which the brand name is "BIOLACTA N5", or "BIOLACTA F N5".

Lactase is also called β-galactosidase. Lactase hydrolyzes β-D-galactoside to produce D-galactose. Lactase also has a classified name, β-D-galactosidegalactohydrolase. Lactase hydrolyzes lactose (glucose-β-D-galactoside) into glucose and galactose.

The activity of an enzyme for transferring sugar to lipid is determined by detecting glycolipids generated by the transferring reaction. The detection may be performed by thin layer chromatography or the like. For example, lactase is added to bread dough in association with lactose and an emulsifier (e.g., monoglyceride); bread is produced; and glycolipids are extracted from the produced bread. In this way, the transferring activity by lactase in a process of producing bread can be determined.

The presence of sugar such as lactose is essential to the transferring activity of the enzyme in the present invention. The sugar such as lactose is naturally contained in a raw material of food products of wheat, and may be further added to the raw material.

The presence of lipid is also essential to the transferring activity of the enzyme in the present invention. Lipid is naturally contained in a raw material of food products of wheat, and may be further added into the raw material. The lipid to be preferably added is a presently available emulsifier for food. In the present invention, a number of fatty acid esters (e.g., monoglyceride) commercially available are used as an emulsifier. Examples of such an emulsifier include "Rheodol" and "Emasol" (brand names; available from Kao Corp.), "EMALGEE MS" (brand name; available from Takeda Chemical Industries, Ltd., produced by Riken Vitamin Co., Ltd.), and "SUN SOFT" (brand name; available from NISSEI KYOEKI Co, LTD.).

The present invention will be described in detail in the case of producing bread. A method of the present invention may be applied to food products of wheat other than bread. The term "food product of wheat" used herein is defined as including breads (e.g., white bread, French bread, snack bread, doughnut, and steamed bread), noodles (raw and dried noodles, e.g., macaroni, pasta, and Japanese vermicelli), confectioneries (e.g., biscuit, cracker, snacks, western-style raw confectioneries, cake, puff pastry, pie, and Japanese-style confectioneries), fried food coated with breadcrumbs, and fried food coated with tempura flour.

Freshness is evaluated for food products of wheat such as bread produced with and without an enzyme as an additive (the latter products are controls). In such an evaluation, the quality of the food products is measured in physical and/or sensory ways a predetermined period of time after being produced. For example, the freshness of bread is evaluated in the following way: bread to which an enzyme has been added is produced; the produced bread is preserved for a predetermined period of time (e.g., 1 to 7 days); and thereafter, hardness, texture, and the like are measured. Those skilled in the art will recognize that evaluation methods and time necessary for evaluation depend on the types of interest of the food products of wheat.

Production of bread is carried out in the following way. Materials of bread dough are mixed together (see Table 1). A purified variant α-amylase is added to the mixture. Fermentation and baking of bread dough are readily carried out by means of a commercially available home bread-baking machine.

The hardness of baked bread is evaluated in the following way. After being baked, bread is preserved for a predetermined period of time in a plastic bag for preventing moisture evaporation as much as possible, and left at room temperature. Thereafter, the hardness of the bread is determined. The measurement of hardness is carried out in the following way. The bread is sliced. A central portion of a slice of the bread is cut out to be a piece in a predetermined size. This piece of the bread is compressed at a predetermined speed while measuring the load necessary for the compression. The maximum load is determined. Additionally, the hardness of the bread may be evaluated by a sensory test.

The present invention will be more specifically described below by way of illustrative examples. The present invention is not limited to these examples.

EXAMPLE 1

Production of Bread with Lactase

Bread was produced by adding lactase to bread dough. Lactase derived from *B. circulans* (this is identical to enzymes of which brand names are "BIOLACTA N5", "BIOLACTA F N5" and the like and commercially available from Daiwa Fine Chemicals Co., Ltd.) and lactase derived from fungi (*Aspergillus oryzae*) (brand name "SUMYLACT", produced by SHIN NIHON CHEMICAL Co., LTD.) were used. "EMALGEE MS" (produced by Takeda Chemical Industries, Ltd.) was used as an emulsifier.

(a) Basic materials for French bread (250 g of hard flour; 30 g of soft flour; 3 g of butter; 5 g of salt; 210 ml of cold water; and 2.2 g of dried yeast); (b) the basic materials and an emulsifier (0.2% by powder, i.e., 0.2% emulsifier against the flour powder (hard+soft)); or (c) the basic materials, the emulsifier (0.2% by powder), lactase (0.2% by powder, corresponding to 1400 LU/g), and lactose (1.2% by powder), was subjected to an automatic bread maker SD-BT150 (produced by Matsushita Electric Industrial Co., Ltd.)

After baking; the bread was left to be cooled at appropriately 21° C. for an hour. Then, the bread was put in a plastic bag for preventing moisture evaporation, and preserved at appropriately 20° C. for 1, 4, or 7 days.

The bread was then sliced into pieces 2 cm thick each. A central portion of each slice of the bread was cut out in 5 cm×5 cm.

Hardness of the bread was measured by the rheometer COMPAC-100 (produced by SUN SCIENTIFIC Co., LTD.)

in the following way: a piece of the bread was compressed by 1 cm at a speed of appropriately 60 mm/min while measuring the load necessary for the compression; and the maximum load is determined. Additionally, the softness and texture of the bread were evaluated by a sensory test. The result is shown in Table 1.

TALE 1

| Sample number | Additive | Hardness | | | Sensory evaluation (Day 4) | |
|---|---|---|---|---|---|---|
| | | Day 1 | Day 4 | Day 7 | Softness | Texture |
| a | none | 365 | 612 | 905 | X | X |
| b | emulsifier | 348 | 525 | 810 | Δ | Δ |
| c | emulsifier + lactase (*B. circulans*) + lactose | 248 | 454 | 520 | ○ | ○ |
| d | emulsifier + lactase (*A. oryzae*) + lactose | 345 | 522 | — | Δ | Δ |
| e | lactase (*B. circulans*) | 264 | 588 | 638 | Δ | Δ |
| f | emulsifier + lactase (*B. circulans*) | 225 | 508 | 621 | Δ | Δ |
| g | lactase (*B. circulans*) + lactose | 191 | 497 | 469 | ○ | ○ |

In Table 1, the softness of bread is represented by ○(soft), Δ(slightly hard), and X(hard); and the texture of bread is represented by ○(smooth), Δ(slightly smooth), and X(non-smooth). The bread with an emulsifier, lactase derived from *B. circulans*, and lactose was compared with the bread without an emulsifier, lactase and lactose; the bread only with the emulsifier; and the bread with the emulsifier, lactase derived from fungi, and lactose. As a result, the bread with an emulsifier, lactase derived from *B. circulans*, and lactose maintains its softness and texture for a longer period of time than the others.

EXAMPLE 2

Analysis of Glycolipids in Bread

1) Extraction of Lipid from Bread

A crumb portion of bread with lactase (and lactose and an emulsifier), or without lactase, produced according to Example 1 was added to 50 mM phosphate buffer (pH 6.0) of 5–10 fold volume relative to the bread, followed by crushing with a homogenizer. The resultant mixture was subject to extraction with the equivalent amount of ethyl acetate in a conventional manner. The ethyl acetate layer was separated by centrifugation, and then collected. The obtained ethyl acetate layer was dried under reduced pressure, followed by dissolving in 2 ml of hexane. Thus, a crude sample of lipids was obtained.

2) Partial Purification of Crude Lipids Using Iatro-beads Column

Iatro-beads were activated in a conventional manner. Iatro-beads (Iatron Laboratories, Inc.) were washed with 0.1 M ammonia water, and then washed with water, followed by adjusting pH to 5–6. Thereafter, Iatro-beads were washed with 0.2 M NaCl, and then washed with water, followed by drying with wind. Iatro-beads were then autoclaved at 105° C. for two days. The resultant Iatro-beads were suspended in a mixture of chloroform, methanol and water with a ratio of 1 to 1 to 0.2, and subjected to ultrasonication to be deaerated. The deaerated Iatro-beads were used for preparing a column (6 mm×3.5 cm) having a bed volume of about 1 ml.

The column was equilibrated with 100% chloroform. The crude sample of lipids obtained in the section 1) was dissolved in 100% chloroform, and adsorbed onto the column. Non-polar lipids were collected with 10 column volumes of 100% chloroform (indicated by I in FIGURE). In similar manners, the eluted fractions were collected with 5 column volumes of a mixture of chloroform and acetone with a ratio of 1 to 1 (indicated by II in FIGURE); 5 column volumes of 100% acetone (indicated by III in Figure): 5 column volumes of a mixture of chloroform and methanol with a ratio of 1 to 1 (indicated by IV in FIGURE): and 5 column volumes of a mixture of chloroform, methanol and water with a ratio of 1 to 1 to 0.2 (indicated by V in FIGURE), respectively.

In this separation operation, monogalactosyldiglyceride (MGDG) was obtained in an eluted fraction of the mixture of chloroform and acetone with a ratio of 1 to 1. Digalactosyldiglyceride (DGDG) and monogalactosylmonoglyceride (MGMG) were obtained in an eluted fraction of the mixture of chloroform and methanol with a ratio of 1 to 1.

3) Analysis of Lipids by Thin Layer Chromatography

Each fraction obtained above was dissolved in a mixture of chloroform and methanol with a ratio of 1 to 1 or a mixture of chloroform, methanol and water with a ratio of 1 to 1 to 0.2. Approximately 3–5 $\mu$g of this mixture was spotted on an HPTLC plate (Merck & Co., Inc., HPTLC Fertigplatten Kieselgel 60). The spot was developed with a developing solvent (a mixture of chloroform, methanol, ammonia water, and water with a ratio of 30 to 20 to 2.4 to 1.2).

After developing, the plate was dried. Then, a solution of 66% (v/v) sulfuric acid containing 0.05% (w/v) anthrone and 1% (w/v) thiourea was sprayed on the plate, followed by heating at 120° C. for coloring. The result is shown in Figure. In Figure, STD indicates monogalactosyldiglyceride (MGDG) (upper band) and digalactosyldiglyceride (DGDG) (lower band) both derived from standard wheat flour. In this method, the Rf value of monogalactosylmonoglyceride (MGDG) is substantially equal to the Rf value of digalactosyldiglyceride (DGDG). The Rf value of monogalactosyldiglyceride (MGDG) is greater than the Rf value of monogalactosylmonoglyceride (MGMG). Moreover, the density of colored bands was converted into numerical values using a computer with Bio Max 1D Image Analysis Software (Kodak).

4) Results

As shown in FIGURE, increases in the density of bands were observed for fraction II and fraction IV when comparing a case where lactase was added (shown by + in Figure) with a case where lactase was not added (shown by − in Figure). According to numerical data obtained by computer, a ratio of the amount of glycolipids in the case where lactase was added to the amount of glycolipids in the case where lactase was not added is 45 to 100 for fraction II, or 60 to 100 for fraction IV. For each fraction, about a two fold increase in glycolipids was observed.

The bands for fraction II and fraction IV, of which density were increased, correspond to monogalactosyldiglyceride (MGDG) and monogalactosylmonoglyceride (MGMG), or digalactosyldiglyceride (DGDG). Thus, it was demonstrated that the added lactase increases glycolipids in bread. It has been known that those glycolipids are useful for maintaining the freshness of bread. Consequently, it is indicated that the quality improvement of bread obtained by addition of lactase as described in Example 1 is due to an increase in glycolipids contained in bread.

EXAMPLE 3

Comparison of the Properties of Lactase Derived from *B. circulans* with Properties of other Lactase)

The activity of lactase derived from *B. circulans* which was used in Examples 1 and 2 was compared with the activity of conventional lactase. Lactase derived from fungi (*Aspergillus oryzae*) (SUMYLACT, SHIN NIHON CHEMICAL Co., LTD.) was used as conventional lactase. Lactase derived from *B. circulans* or lactase derived from fungi was added by 5 or 20 LU/g lactose to a solution of 55% lactose (w/w). The reaction was carried out at pH 6.0 and at 60° C. (for lactase derived from *B. circulans*), or at pH 5.0 and at 50° C. (for lactase derived from fungi), for 20 hours. The amount of lactase required for producing 1 μmol of glucose for one minute at the beginning of reaction when lactase reacts with lactose (final concentration of 10%) at pH 6.0 and at 40° C., is defined as "1 LU", representing the activity of lactase. After the reaction, amounts of various galactooligosaccharides were determined by HPLC analysis. The result is shown in Table 2 (the unit of numeric figure is % in Table 2).

TABLE 2

|  | BIOLACTA | | lactase from fungi | |
| --- | --- | --- | --- | --- |
|  | 5 Lu/g lactose | 20 LU/g lactose | 5 Lu/g lactose | 20 LU/g lactose |
| galactooligo | 54.2 | 59.0 | 32.6 | 34.5 |
| glucose | 22.3 | 21.5 | 19.9 | 30.2 |
| galactose | — | 4.5 | 6.9 | 15.6 |
| disaccharide | 38.8 | 38.0 | 44.0 | 30.7 |
| trisaccharide | 22.2 | 22.2 | 19.6 | 14.6 |
| quadrasaccharide or more | 16.7 | 13.8 | 9.6 | 8.9 |

For lactase derived from fungi, when the amount of the enzyme was increased, glucose and galactose increased while di-, tri-, quadra- and more saccharides decreased. This indicates that the hydrolyzing activity is superior to the transferring activity. For lactase derived from *B. circulans*, even when the amount of the enzyme was increased, the percentage of each saccharide did not substantially change. This means that the latter lactase has the transferring activity as well as the hydrolyzing activity.

Bread obtained by the method for producing food products of wheat according to the present invention is softer, and has improved capability of holding moisture such that its freshness obtained immediately after baking can be maintained for a longer period of time, than bread obtained by a conventional method. Furthermore, the method of the present invention can produce food products of wheat without damaging their materials, whereby the process control becomes easy, and handling and production efficiency are improved.

Various other modifications will be apparent to and can be readily made by those skilled in the art without departing from the scope and spirit of the present invention. Accordingly, it is not intended that the scope of the claims appended hereto be limited to the description as set forth herein, but rather that the claims be broadly construed.

What is claimed is:

1. A method for preparing a wheat food product, the method comprising:

adding a Bacillus lactase enzyme and water to a wheat raw material to create a mixture; and heating the mixture to obtain a wheat food product.

2. The method of claim 1, wherein the Bacillus lactase enzyme is a *Bacillus circulans* lactase enzyme.

3. The method of claim 1, further comprising the step of adding lipids to the wheat raw material prior to the heating step.

4. The method of claim 1, further comprising the step of adding lactose to the wheat raw material prior to the heating step.

5. The method of claim 1, wherein the wheat food product is bread, noodles, confectioneries, fried products with breadcrumbs, or fried products with tempura flour.

6. The method of claim 1, wherein the wheat food product is bread.

7. The method of claim 1, whereby the wheat food product maintains its freshness for a longer period of time than a wheat food product prepared without the addition of the enzyme.

* * * * *